United States Patent [19]

Sholl et al.

[11] 4,229,978

[45] Oct. 28, 1980

[54] SYSTEM FOR SELECTABLY PULSING ULTRASONIC TRANSDUCERS IN A TEST APPARATUS

[75] Inventors: Howard A. Sholl, Storrs; John T. Marshall, Willimantic, both of Conn.

[73] Assignee: Dapco Industries, Inc., Ridgefield, Conn.

[21] Appl. No.: 947,482

[22] Filed: Oct. 2, 1978

[51] Int. Cl.² .............................................. G01N 29/00
[52] U.S. Cl. ........................................ 73/626; 73/632; 310/317; 328/67
[58] Field of Search ................. 73/609, 618, 620, 625, 73/626, 629, 632, 636, 641; 340/1 R, 3 R, 3 A, 5 R, 15; 332/26; 307/252 J, 252 K; 328/67; 310/317, 334, 336

[56] References Cited

U.S. PATENT DOCUMENTS

| | | | |
|---|---|---|---|
| 3,251,220 | 5/1966 | Joy | 73/620 |
| 3,257,637 | 6/1966 | Henry | 73/620 |
| 3,585,405 | 6/1971 | Stettiner | 307/252 J |
| 3,982,425 | 9/1976 | McLain | 73/632 |
| 4,114,457 | 9/1978 | Thun | 73/632 |

Primary Examiner—Stephen A. Kreitman
Attorney, Agent, or Firm—St. Onge, Steward, Johnston, Reens & Noe

[57] ABSTRACT

A system for selectably electrically pulsing each of a plurality of ultrasonic transducers in a testing apparatus in rapid sequence to produce a pattern of ultrasonic energy transmitted into and subsequently received from a test piece comprises a plurality of transducer pulsing circuits, each connected to a different associated one of the transducers. Each pulsing circuit includes a silicon control rectifier connected to ground and a capacitor, connected between the rectifier and the associated transducer, that is dischargeable to pulse the associated tranducer. The rectifier is switchable to an "on" condition to rapidly discharge the capacitor to ground. The rectifier maintains the "on" condition until current conducted through it drops below a characteristic holding current and thereafter switches to an "off" condition. A two-state regulated voltage source is connected to the junction between the rectifier and the capacitor in each of the pulsing circuits to provide a proper charging source for the capacitor. The regulated voltage source is maintained in a high-impedance, voltage-source state designed to maintain an existing capacitor charge in spite of device leakage currents while maintaining a current level less than the rectifier holding current. Individual capacitors are isolated by a diode "and" network in the charging current path. A quick recharge, current-source state is established to recharge the capacitors at a controlled rate to a regulated voltage level. When the desired voltage is reached, the regulated voltage source reverts to its voltage-source state to maintain the voltage until the next such cycle of operation.

7 Claims, 2 Drawing Figures

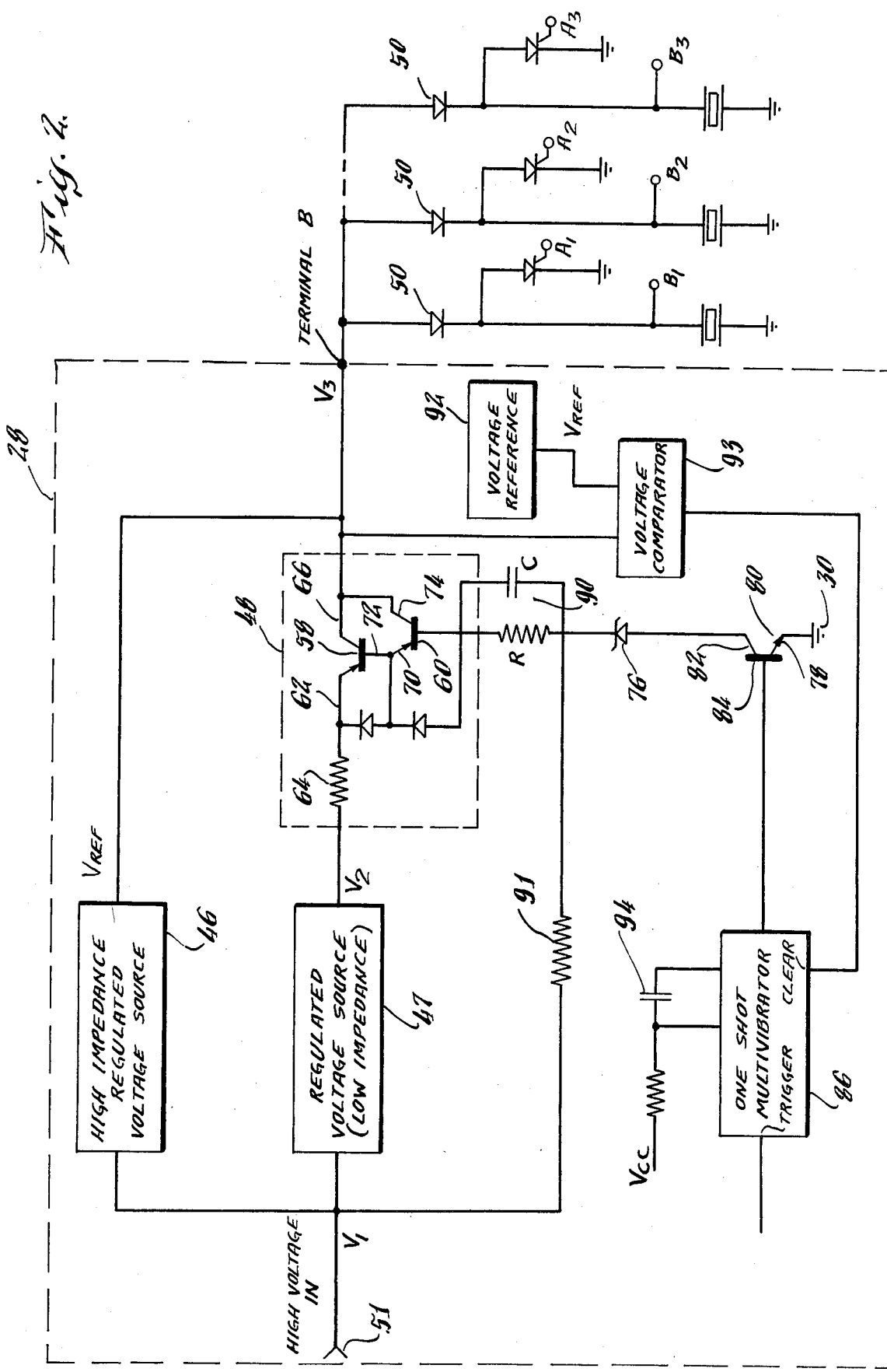

SYSTEM FOR SELECTABLY PULSING ULTRASONIC TRANSDUCERS IN A TEST APPARATUS

BACKGROUND OF THE INVENTION

The present invention relates to a system for selectably electrically pulsing each of a plurality of ultrasonic transducers in a non-destructive testing apparatus in rapid sequence. This system is well suited for use with testing apparatus, such as ultrasonic rail testing apparatus, that includes a plurality of transducers for producing a pattern of ultrasonic energy transmitted into and subsequently received back from the rail to thoroughly probe all portions thereof.

Various systems for ultrasonically inspecting test pieces are known. Such a system for inspecting a test piece, specifically a railroad rail, is disclosed in U.S. patent application Ser. No. 818,544, now U.S. Pat. No. 4,165,648, (Pagano) and includes leading and trailing ultrasonic inspection wheels adapted to roll on a railroad rail in spaced relation. An array of ultrasonic transducers is mounted in each inspection wheel and includes two transducers looking laterally of the rail, three transducers looking longitudinally, one transducer looking normally and one send/receive transducer. The send/receive transducer in the leading wheel operates in cooperation with the similar transducer in the trailing wheel to transmit ultrasonic energy thereto and receive ultrasonic energy therefrom in an alternating send/receive mode. Each of the transducers in the leading and trailng wheels is independently capable of transmitting ultrasonic energy, through a suitable coupling medium in the wheel, into the rail and of receiving ultrasonic energy transmitted back thereto to produce an individual response signal.

In order to operate such a rail testing apparatus at high speed to inspect the rail with a known recurring pattern of ultrasonic energy, it is necessary to be able to rapidly pulse the transducers in a known sequence chosen to minimize interference between the ultrasonic pulses generated by them as well as to rapidly recycle each transducer for subsequent pulsing.

In prior art ultrasonic testing apparatus employing a plurality of transducers, capacitors have been used to provide the pulsing power for each transducer. However, it has been found that when the transducers are rapidly pulsed in sequence, a voltage drop occurs across the capacitor or capacitors used to pulse the transducers, thereby limiting the rapidity with which the transducers may be recycled for driving.

SUMMARY OF THE INVENTION

In its preferred embodiment, the present invention comprises a system for selectably electrically pulsing subsets of a plurality of ultrasonic transducers in an ultrasonic testing apparatus in rapid sequence. This system permits the transducers to be recycled quickly for subsequent pulsing and further permits rapid sequential pulsing of the plurality of transducers in the apparatus. Accordingly, an apparatus such as the rail testing apparatus disclosed in U.S. patent application Ser. No. 818,544 (Pagano) may be operated at high speed to rapidly inspect a test piece.

In the preferred embodiment, the system of the present invention includes a plurality of transducer pulsing circuits, each connected to a different associated one of the transducers. Each pulsing circuit includes a silicon controlled rectifier connected to ground and a capacitor connected between the rectifier and the associated transducer. Each capacitor may be discharged to pulse its associated transducer and the associated rectifier is switchable under the control of a control computer to an "on" condition to permit this rapid discharge. Further, the rectifier maintains the "on" condition until current conducted through it drops below a characteristic holding current. Thereafter, the rectifier switches to an "off" condition.

The rectifier provides a particularly useful switching device that can be operated at high efficiency with low power requirements. However, if the rectifier is not reliably switched to the "off" condition, current supplied to the circuit to charge the capacitor is merely short circuited to ground. That is, if rapid charging of the capacitor is attempted with a low impedance voltage source at high current above the rectifier holding current, the rectifier does not switch "off" and charging is inefficient. However, if charging of the capacitor is attempted with a high impedance voltage source at low current below the holding current of the rectifier, the rectifier will switch to the "off" condition but capacitor charging will be undesirably slow.

Thus the following mode of operation is used. During the firing of a desired subset of rectifiers and immediately thereafter the voltage regulator maintains its high impedance, voltage-source state for a time interval bounded by the occurrence of another signal whose function is to change the regulator state to a current source for recharge purposes. The state change may thus be positioned to occur either before or after the desired time interval in which the transducer echoes are being received. The state change must, however, be delayed at least a time interval sufficient to guarantee that the fired rectifiers have switched to the "off" condition. Since the initial high impedance, voltage-source state has a maintaining current less than the holding current of the rectifiers, rectifier turn-off is insured. When the current-source state is established, the discharged capacitors recharge at a constant rate defined and controlled by the regulator. In this manner a maximum recharge rate is established which avoids the common problem of undesirable refiring due to an excessive charging rate. When the voltage level of the charging capacitors reaches the desired level, the regulator reverts to its high impedance, voltage-source state, to maintain the charge until another firing has occurred.

Accordingly, it is an object of the present invention to provide a system for rapidly sequentially pulsing a plurality of transducers in an ultrasonic transducer testing apparatus. It is a further object of the invention to provide such a system which recharges a subset of capacitors for pulsing a subset of transducers in a interval unique from the discharge of another capacitor subset.

It is a further object of the invention to provide a system for selectably electrically pulsing the transducers in an ultrasonic testing apparatus in which charging of each capacitor after discharge is accomplished without loss of charging current to enhance the speed with which each capacitor is charged.

Other objects, features and advantages of the present invention will be pointed out in, or will be understood from, the following detailed description provided below in conjunction with the accompanying drawings.

BRIEF DESCRIPTION OF THE DRAWINGS

FIG. 2 is a schematic diagram of the system.

DETAILED DESCRIPTION OF THE PREFERRED EMBODIMENT

Figure 1:
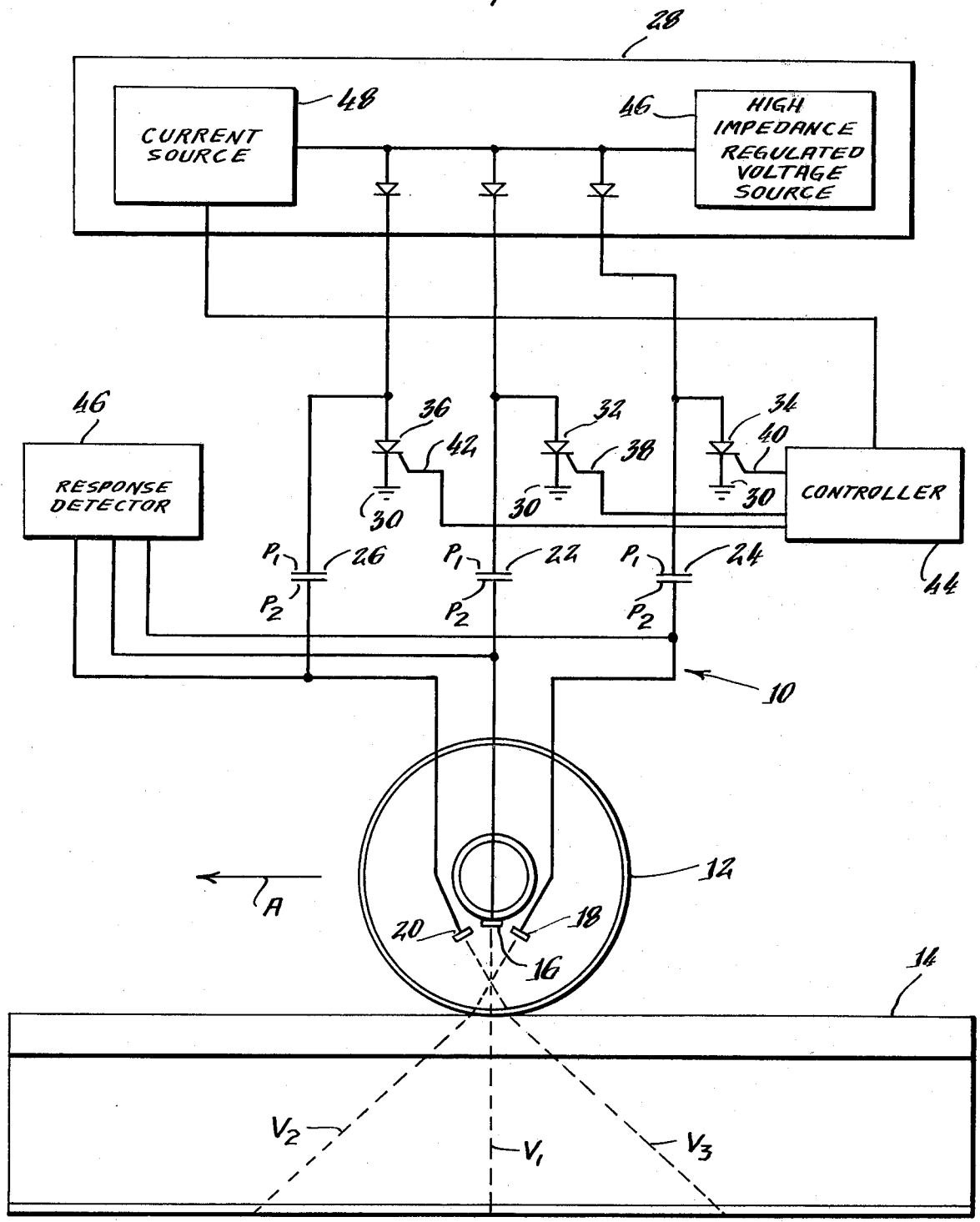
FIG. 1 is a diagrammatic representation of the system for selectively pulsing each of a plurality of transducers in an ultrasonic testing apparatus.

As shown in FIG. 1, the system of the present invention, generally indicated at 10, is adapted for use with an inspection apparatus which employs ultrasonic transducers to probe a test piece with ultrasonic energy. For convenience, the inspection apparatus is illustrated as a railroad rail inspection wheel 12 adapted to be rolled at high speed, in the direction of arrow A, in contact with a test piece in the form of a railroad rail 14 in order to transmit ultrasonic energy into and receive ultrasonic energy back from the rail. The inspection wheel includes a plurality, specifically three ultrasonic transducers, a first 16 of which is mounted to emit a beam $U_1$ of ultrasonic energy conducted through a suitable coupling medium in the wheel and then perpendicularly into the rail. A second transducer 18 is mounted to emit a beam $U_2$ of ultrasonic energy that is conducted forwardly into the rail and a third transducer 20 is mounted to emit beam $U_3$ that is conducted rearwardly into the wheel. While only three transducers are illustrated, it is to be understood that the system of the present invention may be employed with inspection apparatus that include many more than three transducers such as that described in U.S. patent application Ser. No. 818,544 (Pagano).

In accordance with the present invention, each transducer is electrically pulsed to emit its respective beam of ultrasonic energy and is subsequently monitored to detect ultrasonic energy reflected back thereto. Moreover, the transducers are pulsed rapidly in a known sequence to probe the rail with a pattern of energy, the sequence being selected to minimize interference between the transducers, to achieve a desired special effect, or for any other desired reason.

In accordance with the system 10, transducer 16 is driven with large pulses supplied through a capacitor 22 connected in series therewith. Similarly, transducer 18 is driven through a capacitor 24 and transducer 20 is driven through a capacitor 26, each transducer and capacitor pair also being connected in series. One plate $P_1$ of each capacitor 22, 24 and 26 is chargeable to high voltage by a switched regulator 28, supplying a charging current as will be described in greater detail below.

The charged plate $P_1$ of each capacitor is discharged to ground 30 when an associated silicon controlled rectifier (SRC) is rendered conductive by a control pulse from control computer 44 and applied to a control electrode of the SCR, capacitor 22 being controllably discharged by SCR 32, capacitor 24 by SCR 34, and capacitor 26 by SCR 36. Each SCR 32, 34 and 36 has a gate control electrode 38, 40 and 42 respectively, to render the rectifier conductive. When conductive, a rectifier rapidly discharges its associated capacitor plate $P_1$. The capacitor transfers this large change to the opposite capacitor plate $P_2$ and thus delivers a pulse to the associated transducer to be pulsed. The control computer is programmed to sequentially pulse the transducers in subsets of one or more transducers, as described above in the chosen sequence.

Ultrasonic energy received by each transducer back from the rail 14 causes the receiving transducer to produce a response signal which is detected by a response detector 46.

Each SCR 32, 34 and 36 has a characteristic holding current above which the SCR conducts and below which the SCR switch becomes nonconductive.

It has been found that the recharging efficiency may be improved by utilizing a high impedance voltage-source to maintain a desired voltage level at a current level below the rectifier holding current; utilizing a current source over a controlled time interval to provide a maximum rate recharging source; and utilizing a voltage comparator function to turn off the current source when the desired voltage level has been achieved. Since a diode "and" function is utilized to achieve capacitor isolation, a single switched-regulator system may be utilized to control a large number of pulsing circuits. The efficiency is improved, therefore, by using a single switched-regulator to control many pulsing circuits in a two-state operating mode to allow reduction and control of the recharging time intervals. Therefore, the present invention, as shown in FIG. 1, includes the switched-regulator 28 for charging each capacitor that comprises a high impedance voltage source 46 which maintains each capacitor at a desired voltage level at a current below the holding current of each silicon controlled rectifier. Therefore, the rectifier turns to its "off" condition permitting all subsequent current to be utilized in charging the associated capacitor. A current source 48, which is capable of rapidly charging each capacitor at high constant current, is switched on by a switching network after the rectifier has turned to its "off" condition. Therefore, subsequent charging of the capacitor subset to its fully charged condition ready for pulsing its associated transducer subset may be accomplished at a rapid rate.

FIG. 2 shows a suitable circuit for the switched regulator 28 described above. As shown there, the high impedance charging source 46 is connected to a junction between the collector 66 of a first transistor 58 and a terminal B leading to a diode array 50. The short circuit current of this source 46 has a value sufficiently low so that the current through the silicon controlled rectifiers is less than the rectifier holding current to ensure that the rectifier turns to its "off" condition, and sufficiently high to compensate for leakage currents from the fully charged capacitors. The open circuit voltage of this source 46 has a value equal to the desired final charging voltage.

The charging source 48 includes a common emitter darlington transistor regulator comprised of the first and a second transistor 58 and 60 respectively. The first transistor has its emitter 62 connected through a resistor 64 to a regulated voltage source 47. The collector 66 of the first transistor is connected to terminal B leading to a diode array 50. The second transistor 60 has its emitter 70 connected to the base 72 of the first transistor, its collector 74 connected to the collector 66 of the first transistor and its base connected to an RC switching network 90 which is, in turn, connected to zener diode 76 and resistor 91 which connects to a high voltage source 51. The voltages in the switched regulator are established such that $V_1 > V_2$, $V_1$ being the high input voltage of source 51 and $V_2$ being the output voltage of the regulated voltage source 47.

Moreover, the current source components and sources of voltages $V_1$ and $V_2$ are chosen so that the capacitor charging rate is sufficiently high to charge any capacitor at a rate slightly less than the rate which would cause undesirable triggering of an associated SCR causing it to conduct.

The transistors 58 and 60 are controlled by a third transistor 84 having its emitter 80 connected to ground 30, its collector 82 connected to zener diode 76 and its base connected to a one-shot multivibrator 86. The third transistor-multivibrator constitutes a switching network that applies a base bias to the first transistors to turn on the current source 48 when desired. The multivibrator is of the one-shot type and controls the charging time during which the current source is active. A feedback network consisting of voltage reference 92, which generates a voltage $V\ ref < V_2$, and voltage comparator 93 is connected to the one-shot multivibrator 86, and to terminal B. When the voltage at terminal B, $V_3$ has risen during charging to the reference voltage value 92, voltage comparator 93 resets the one-shot multivibrator 86 to turn off the current source. Furthermore, network 94 connected to one-shot multivibrator 86 provides a maximum time interval for the charging period. Its function is to prevent circuit component damage if a malfunction occurs in the feedback network.

The high impedance source is maintained in "on" condition at all times during system operation. Therefore, the switching network controls the current source to switch on at appropriate timed intervals in the operation of the tranducer array so that the charging of each capacitor for subsequent pulsing of its associated transducer may be accomplished in the required time.

Accordingly, it will be appreciated that the system of the present invention permits rapid sequential charging of subsets of capacitors for pulsing in rapid sequence subsets of transducers used in an ultrasonic inspection apparatus. Moreover, because of the use of the silicon controlled rectifiers for operation of capacitors controlling pulsing of each transducer, and because of the unique combination of current source and high impedance voltage source in the switched regulator, positive charging of the driving capacitors may be achieved while minimizing unwanted variations of voltage while utilizing a single switched regulator. Accordingly, although a specific embodiment of the present invention has been described above in detail, it is to be understood that it is for purposes of illustration. Modifications may be made to the described system in order to adapt it to particular ultrasonic testing applications.

What is claimed is:

1. A system for selectably electrically pulsing subsets of at least one of a plurality of ultrasonic transducers in a testing aparatus in rapid sequence to produce a pattern of ultrasonic energy transmitted into and subsequently received from a test piece, said system comprising:
    a plurality of transducer pulsing circuits, each connected to a different associated one of said transducers and including charge storing means dischargeable to electrically pulse said associated transducer and electronic switch means connected between said charge storing means and ground, said electronic switch means being switchable to an "on" condition to rapidly discharge said charge storing means, said electronic switch means further maintaining said "on" condition until current conducted thereby drops below a characteristic holding current and thereafter switching to an "off" condition; and
    switched regulator means connected to each of said pulsing circuits for recharging said charge storing means therein, including a high impedance source of voltage for maintaining a desired charge on said charge storing means at a current less than said holding current thereby allowing said electronic switch means to switch to the "off" condition and a regulated current source for rapidly charging said charge storing means after said electronic switch means is switched to the "off" condition.

2. A system for selectably electrically pulsing subsets including at least one of a plurality of ultrasonic transducers in a testing apparatus in rapid sequence to produce a pattern of ultrasonic energy transmitted into and subsequently received from a test piece, each of said transducer subsets being operable by a control computer that determines said sequence, said system comprising:
    a plurality of transducer pulsing circuits, each connected to a different associated one of said transducers and including a silicon controlled rectifier connected to ground and a capacitor, connected between said rectifier and said associated transducer, that is dischargeable to pulse said associated transducer, said rectifier being switchable to an "on" condition under the control of said control computer to rapidly discharge said capacitor to ground, said rectifier maintaining said "on" condition until current conducted thereby drops below a characteristic holding current and thereafter switching to an "off" condition;
    means for supplying a voltage at high impedance connected to the junction between said rectifier and said capacitor in each of said pulsing circuits for maintaining a desired charge on said capacitor therein at a low current less than said holding current, thereby allowing said rectifier to switch to the "off" condition;
    means for supplying a current also connected to the junction between said rectifier and said capacitor in each of said pulsing circuits for rapidly charging said capacitor therein at high current; and
    means for switching on said current supplying means after said rectifier is switched to said "off" condition;
    means for isolating each said capacitor in each of said pulsing circuits for allowing isolation between each said capacitor; and
    means for switching off said current source after said capacitor subset has achieved a desired voltage level of charge.

3. The system of claim 2 wherein said current supplying means operates at a charging rate sufficiently high to charge said capacitor at a rate just below that rate which would cause undesirable triggering of said associated rectifier.

4. The system of claim 2 wherein said current supplying means comprises a source of regulated voltage and a common-emitter darlington transistor regulator network including first and second transistors, said first transistor having a collector connected to said junction of said rectifier and said capacitor and an emitter connected to said source of current, said second transistor having an emitter connected to the base of said first transistor, a collector connected to the collector of said first transistor, and a base connected to said switching means.

5. The system of claim 4 wherein said switching means comprises a third transistor having a collector connected to said base of said second transistor, and an emitter connected to ground, and a one-shot multivibrator connected to the base of said third transistor.

6. The system of claim 5 further comprising a feedback network including means for generating a reference voltage, V ref, and means for comparing said reference voltage with the voltage generated by said current supplying means $V_3$ during capacitor charging and when $V_3 \geqq V$ ref resetting said multivibrator to turn off said current supplying means.

7. The system of claim 5 further comprising means for limiting the time during which said capacitor may be charged by said current supplying means.

* * * * *